Figure 1:
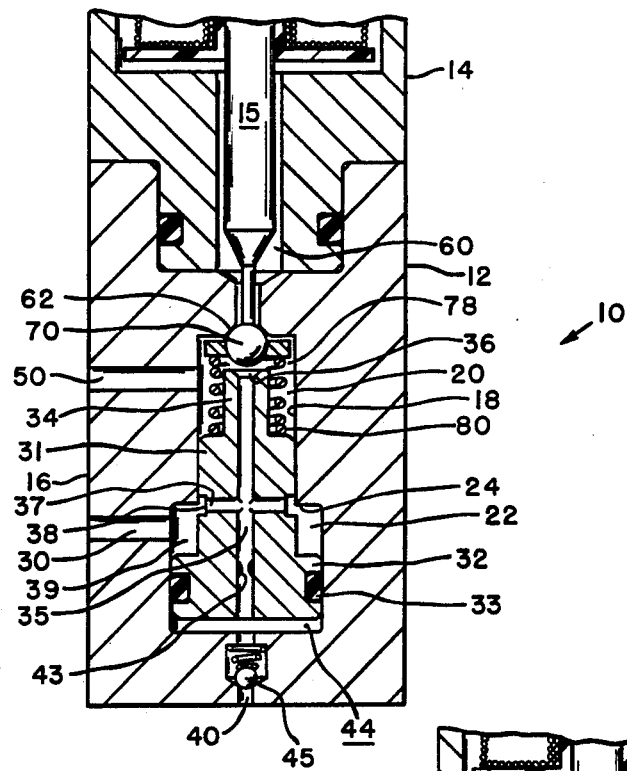

United States Patent [19]

Martinic

[11] Patent Number: 4,844,119
[45] Date of Patent: Jul. 4, 1989

[54] INTEGRATED THREE-WAY AND ISOLATION SOLENOID VALVE

[75] Inventor: Jack Martinic, South Bend, Ind.
[73] Assignee: Allied-Signal Inc., Morristown, N.J.
[21] Appl. No.: 274,076
[22] Filed: Nov. 21, 1988
[51] Int. Cl.[4] ............... B60T 8/36; F15B 13/044
[52] U.S. Cl. ............... 137/596.17; 137/625.65; 251/129.14; 303/113; 303/119
[58] Field of Search ............ 137/596.17, 625.65; 251/129.14; 303/61, 113, 114, 115, 116, 117, 119

[56] References Cited
U.S. PATENT DOCUMENTS
4,620,565 11/1986 Brown ............... 137/596.17

Primary Examiner—Duane A. Reger
Attorney, Agent, or Firm—Larry J. Palguta; Ken C. Decker

[57] ABSTRACT

A control valve (10) comprises a valve assembly (12) having a stepped bore (18) which communicates with a first inlet (30) from a master cylinder, a second inlet (40) from a pump, a first outlet (50) to a wheel brake, and a decay outlet (60) permitting fluid flow away from the first outlet (50) during decay of fluid pressure for anti-lock operation. A first valve element (31) comprises a reduced diameter section (20) extending into an enlarged diameter section (22) which is received within a correspondingly shaped enlarged diameter section (32) of the bore (18). The first valve element (31) includes a longitudinal through passage (35) with a restriction (43) therein, and a transverse fluid passage (37) which intersects the longitudinal through passage (35) and communicates with the enlarged diameter section (22) of the stepped bore (18). One end of the first valve element (31) comprises a valve seat (36) disposed adjacent a second valve element (70) that is operated by an actuator (14). A spring (80) extends between the first valve element (31) and second valve element (70) to bias the second valve element (70) toward a closed position at a valve seat (62) of the decay outlet (60). The first inlet (30) communicates fluid pressure from the master cylinder to the enlarged diameter section (22) of the bore (18) to effect fluid communication with the longitudinal through passage (35) separate from fluid pressure received from the pump and communicated through the second inlet (40) to a separate receiving chamber (44) defined between the enlarged diameter sections (22, 32) of the first valve element (31) and stepped bore (18).

12 Claims, 1 Drawing Sheet

INTEGRATED THREE-WAY AND ISOLATION SOLENOID VALVE

The present invention relates to valves for controlling the flow of a fluid such as hydraulic brake fluid, and particularly to a solenoid actuated valve which functions both as a three-way valve and as an isolation valve, such a valve having particularly advantageous application in an anti-lock braking system.

In various fluid power systems, there exists a need for controlling the application of pressurized fluid between a source of such fluid and an actuator. It has been a common practice to provide a solenoid valve and an associated control device to accomplish this purpose. One particularly relevant application of such valves is in an anti-lock braking system in which control of the applicaiton of pressurized fluid to wheel brakes (pressure build), release of pressurized brake fluid from the wheel brakes (decay), and isolation of the wheel brakes from the source of pressurized fluid (isolation) are controlled by multiple solenoid valves and an electronic control device responsive to rotational movement of a vehicle wheel. Such systems are disclosed in numerous U.S. patents and are now well known to those skilled in the art. It is apparent that the cost and reliability of such systems is affected adversely by a number of solenoid valves required to control the flow of braking fluid, the result of not only the number of valves required but also the number of interconnecting fluid lines, solenoid control outputs, wiring, and the like. Accordingly, it is highly desirable to develop a solenoid actuated control valve for use in pressurized fluid systems which enables a reduction of the number of solenoid valves required. Brown U.S. Pat. No. 4,620,565 entitled "Integrated Three-Way and Isolation Solenoid Valve" and assigned to the same assignee as herein, discloses a solenoid-actuated control valve which accomplishes the desired objectives described above. However, it is desirable to provide a further improved valve which is not subject to sudden high pressure increases from the master cylinder which may result from a spike application of the brakes and which can cause first valve means therein to be moved to a position where fluid flow is through an orifice restriction. It is also desirable of the first valve means will provide isolation of fluid flow from the master cylinder so that a check valve in a fluid flow line from the master cylinder may be eliminated. It is also desirable to provide a solenoid actuated valve wherein a bypass line with a check valve may be eliminated so that during the release phase of braking the valve permits return flow to the master cylinder without the need of such bypass line and check valve. Finally, it is desirable to provide a solenoid actuated valve which shuttles reliably as predicted.

The present invention provides solutions to the above problems by disclosing a control valve comprising a valve body having a bore and a first inlet, second inlet, a first inlet, and a decay outlet, first valve means received reciprocally in said bore and having a longitudinal through passage therethrough communicating between said second inlet and said outlets, second valve means normally closing said decay outlet and displacable to an open position and further to cooperate with said longitudinal through passage and thereby cause a fluid pressure differential across said first valve means, a transverse opening extending through said first valve means to intersect said longitudinal through passage and provide communication between said first inlet and the outlets, said first valve means being moveable in response to the fluid pressure differential thereacross to be displacable to a displaced position wherein flow between said first inlet and said transverse passage is terminated so that fluid may flow between said second inlet and outlets, and actuator means for moving said second valve means from a closed position to an open position in response to said control signals.

Figure 2:
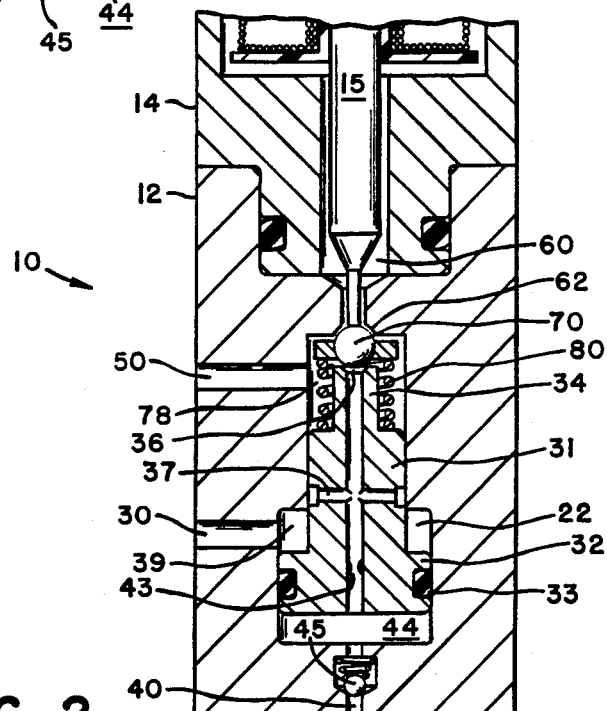

One way of carrying out the invention is described in detail below with reference to the drawings which illusrate an embodiment in which:

FIG. 1 illustrates the solenoid actuated valve with the present invention during normal braking; and FIG. 2 illusrates the solenoid actuated valve during anti-lock braking operation.

Referring now to the drawings and in particular to FIG. 1, there is shown an integrated three-way and isolation solenoid valve in accordance with the present invention and indicated generally by reference numeral 10, which includes a valve assembly 12 and a solenoid actuator 14 with an actuator rod 15. Valve assembly 12 includes a valve body 16 having a cylindrical stepped bore 18. Stepped bore 18 includes a reduced diameter section 20 which communicates with an enlarged diameter section 22. Located between the reduced and enlarged diameter sections is a shoulder 24. A first inlet 30 communicates fluid pressure from a master cylinder (not shown) and a second inlet 40 receives fluid pressure from a pump (not shown). Each of the inlets communicates with the enlarged diameter section 22. Second inlet 40 includes a one-way flow valve means or check valve 45. A first outlet 50 communicates the reduced diameter section 18 with a wheel brake (not shown), and a decay outlet 60 communicates the reduced diameter section with a decay circuit of an antilock braking system (not shown). Decay outlet 60 provides a decay valve seat 62. Received within stepped bore 18 is a first valve element 31 which includes a reduced diameter section 34 and an enlarged diameter section 32. Disposed about enlarged diameter section 32 may be a seal 33. Extending longitudinally through valve element 31 is a longitudinal through passage 35 which terminates in a valve seat 36 at one end of the first valve element. Disposed within longitudinal through passage 35 is a fluid flow restriction 43. Located adjacent seat 36 and closing valve seat 62 during normal braking operation, is a second valve element 70 which is biased by resilient means 80 extending between second valve element 70 and a shoulder of first valve element 31. Valve element 70 and resilient means 80 are located in valve chamber 78. Extending transversely through valve element 31 is a transverse fluid passage 37 which intersects the longitudinal through passage 35 and is disposed adjacent shoulder 24. Transverse passage 37 communicates with a valve groove 38. Enlarged diameter section 22 of bore 18 defines with the enlarged diameter section 32 of first valve element 31 a fluid receiving chamber 44 which communicates with the second or pump inlet 40. Enlarged diameter sections 22, 32, and shoulder 24 define a fluid receiving chamber 39 which communicates with the first of master cylinder inlet 30. Fluid receiving chamber 39 communicates, during normal braking, with groove 38 and transverse fluid passage 37, while fluid receiving chamber 44 communicates with longitudinal through passage 35.

The prsent invention provides an improved solenoid actuated valve as compared to previous systems such as that disclosed in copending Ser. No. 50,350, now U.S. Pat. No. 4,794,267, entitled "Anti-Lock Braking System Check Valve With Build Orifice" and assigned to the same assignee as herein, and Brown U.S. Pat. No. 4,620,565, both the copending patent application and issued patent being incorporated herein by reference. During normal braking operation, fluid braking pressure is received through first inlet 30 and communicates with pressure receiving chamber 39. The fluid pressure is communicated through transverse fluid passage 37, longitudinal through passage 35, past valve seat 36, and through first outlet 50 to the associated wheel brake or wheel brakes. In case of a sudden spike apply of the brakes, instead of the fluid pressure received at master cylinder inlet 30 causing the first valve element 31 to move upwardly so that fluid flow may be through an orifice restriction, which is undesirable, the sudden high fluid pressure received in chamber 39 causes first valve element 31 to move downwardly in FIG. 1 so that fluid flow may pass freely through transverse passage 37, longitudinal through passage 35, and to the wheel brakes. During normal braking operation, the second valve element 70 closes valve seat 62. During anti-lock brake operation, the electronic control unit (not shown) of the system will immediately activate the pump (not shown) so that fluid pressure is received through the second inlet 40 and into chamber 44. This causes the first valve element 31 to move upwardly in bore 18, to a position wherein shoulder 24 of stepped bore 18 closes off or substantially restricts fluid flow between fluid receiving chamber 39 and transverse fluid passage 37 (see FIG. 2). Fluid pressure within receiving chamber 44 is communicated through longitudinal through passage 35, via restriction 43, past valve seat 36 and through first outlet 50 to the wheel brake or wheel brakes. This describes the pressure build mode of anti-lock braking system operation. As the anti-lock braking system determines via a wheel speed sensor or sensors that brake fluid pressure should be released from the wheel brake(s) in order to prevent wheel lockup, the electronic control unit signals actuator 14 which operates to displace actuator rod 15 against second valve element 70 to move element 70 downwardly toward, and in some cases into engagement with, valve seat 36. This opens decay outlet 60 and permits fluid pressure to flow into the decay circuit. As fluid pressure is received within valve chamber 78 by reason of decay outlet 60 being open and second valve 70 stopping or restricting the flow of pressurized fluid through longitudinal through passage 35, the fluid pressure in chamber 78 reduces to a value less than the pressure of pressurized fluid at second inlet 40 plus a pressure force value equal to the force exerted by spring 80 against first valve element 31, and when solenoid 14 is deenergized, first valve element 31 will slide upwardly in stepped bore 18 to bring valve seat 36 toward engagement with second valve 70 to stop or restrict fluid communication between the second inlet 40 and the outlet 50. The upward movement of first valve element 31 is less than the initial available axial movement of second valve element 70 such that when valve element 31 is in its upward position, second valve element 70 is still capable of axial movement between a position closing decay port 60 and a position closing longitudinal through passage 35. Valve element 31 will remain in the upward position as long as the force from pressure in chamber 78 plus the force exerted by the spring 80 is less than the force exerted by pressurized fluid in pressure receiving chamber 44 when solenoid valve 14 is deenergized. When solenoid 14 is energized, the additional force may momentarily overcome the differential pressure force. However, fluid flow is still shut off by the second valve element 70. Second valve element 70 may be cycled between open and closed positions as desired by means of appropriate control signals to the actuator 14. The stroke and corresponding movement of valve element 70 is reduced significantly when the valve element 31 is in its upper position. Accordingly, while response of the valve will be slower during a first cycle when valve element 31 moves from its lower to its upper position, the response by the valve will increase thereafter. When second valve element 70 is seated against decay valve seat 62, fluid pressure will rise at a controlled rate in chamber 78 by reason of the restriction 43 within longitudinal through passage 35. If valve element 70 remains seated against decay valve seat 62, the pressure in chamber 78 will eventually reach a pressure sufficient to allow spring 80 to force first valve element 31 back to its lower position thereby reopening the transverse fluid passage 37.

The control valve of the present invention provides substantial advantages over prior control valves. In case of a spike apply of the brakes, the fluid pressure received from the master cylinder will not force first valve element 31 into a displaced position wherein fluid flow to the brakes is through an orifice restriction. Rather, the fluid pressure from the master cylinder will cause the first valve element 31 to move downwardly so that fluid may flow freely through transverse opening 37, longitudinal through opening 35, and to outlet 50. Prior anti-lock braking systems typically used a check valve in order to effect isolation in the circuit between the master cylinder and solenoid actuated valve mechanism so that during anti-lock braking, fluid pressure could not be transmitted to the master cylinder. The solenoid actuated valve accomplishes this by means of the closure of transverse fluid passge 37 so that fluid pressure from the pump received in chamber 44 is not communicated to chamber 39 and out through first inlet 30. Therefore, communication with the master cylinder is effectedly isolated during anti-lock operation. Additionally, during the release phase of braking, prior anti-lock brake circuits provided a bypass line with a check valve for return flow to the master cylinder. This has been eliminated by having the master cylinder inlet disposed separate from the pump inlet so that during the release phase of braking fluid may flow back through inlet 30 and toward the master cylinder. Also, the shuttling effect of first valve element 31 is now provided in a predictable and reliable manner. During anti-lock braking operation, fluid pressure is received in chamber 44 and communicated through longitudinal through passage 35 via restriction 43. This effects a positive shuttle of the first valve element 31 in a predictable and reliable manner. Control valve 10 of the present invention also may be utilized with solenoid valve 14, or it can be installed separately. Another advantage of the present invention is that in case first valve element 31 should become stuck in the isolated position (displaced upwardly), increased master cylinder pressure communicated to receiving chamber 39 will force valve element 31 to be displaced downwardly so that master cylinder communication with the brakes is open. The control valve of the present invention provides a one way flow valve means of check valve 45 which prevents any fluid displacement effected by the master cylinder from being communicated into the pump and accumulator circuit. Such as valve is important in the event of a total or partial loss of the accumulator's gas charge or a faulty check valve in the pump. The orifice 43 is disposed within the circuit such that it is in line with fluid flow when the pump is actuated.

The present invention provides isolation of the measter cylinder at minimal cost, and effects shuttling of the first valve element by means of the on-and-off actuation of the pump. This eliminates the prior usage of return springs which has to be balanced in order to move appropriately the valve element. Additionally, seal 33 may be provided at the enlarged diameter section 32 of valve element 31. However, other seals are not required. The diametrical clearances can provide for adequate isolation.

Various modifications of the above-described embodiment of the invention will be apparent to those skilled in the art. It is to be understood that such modifications can be made without departing from the scope of the invention.

I claim:

1. For use in an anti-lock braking system which includes a source of pressurized braking fluid, wheel braking means, and an anti-lock control means for generating brake control signals in response to behavior of a wheel, a control valve comprising a valve body having a bore and a first inlet, second inlet, a first outlet, and a decay outlet, first valve means received reciprocally in said bore and having a longitudinal through passage therethrough communicating between said second inlet and said outlets, second valve means normally closing said decay outlet and displacable to an open position and further to cooperate with said longitudinal through passage and thereby cause a fluid pressure differential across said first valve means, a transverse opening extending through said first valve means to intersect said longitudinal through passage and provide communication between said first inlet and the outlets, said first valve means being moveable in response to the fluid pressure differential thereacross to be displacable to a displaced position wherein flow between said first inlet and said transverse passage is terminated so that fluid may flow between said second inlet and outlets, and actuator means for moving said second valve means from a closed position to an open position in response to said control signals.

2. The control valve in accordance with claim 1, wherein said longitudinal through passage comprises restriction means therein.

3. The control valve in accordance with claim 1, wherein said bore includes a shoulder therein, said shoulder comprising means for closing said transverse fluid passage.

4. The control valve in accordance with claim 1, wherein said second inlet includes therein one way fluid flow valve means.

5. The control valve in accordance with claim 1, wherein resilient means is disposed within said bore and biases said first valve means toward a first position.

6. The control valve in accordance with claim 5, wherein said actuator means comprises an electric solenoid having a plunger, said plunger engagng said second valve element.

7. The control valve in accordance with claim 6, wherein said longitudinal through passage communicates between a valve seat and an end of said bore, said valve seat being positioned adjacent said second valve means.

8. The control valve in accordance with claim 1, wherein said bore comprises a stepped bore, said first valve means having an enlarged diameter section received within an enlarged diameter section of said stepped bore, the enlarged diameter section of the first valve means, the valve body, and a shoulder of said stepped bore defining a first receiving chamber communicating with said first inlet.

9. The control valve in accordance with claim 8, wherein during a release phase of braking, fluid may flow from said first receiving chamber through said first inlet and toward a master cylinder.

10. The control valve in accordance with claim 8, wherein said enlarged diameter section of the first valve means and an end of said stepped bore define therebetween a second fluid receiving chamber communicating with said second inlet.

11. The control valve in accordance with claim 10, wherein the resilient means biases second valve element toward a closed position.

12. The control valve in accordance with claim 1, wherein said first inlet comprises a master cylinder inlet, said second inlet comprises a pump inlet, and said first outlet comprises an outlet to said wheel braking means.

* * * * *